United States Patent [19]

Weinblatt

[11] 4,075,657
[45] Feb. 21, 1978

[54] EYE MOVEMENT MONITORING APPARATUS

[76] Inventor: Lee S. Weinblatt, 797 Winthrop Road, Teaneck, N.J. 07666

[21] Appl. No.: 773,899

[22] Filed: Mar. 3, 1977

[51] Int. Cl.² .............................................. H04N 7/18
[52] U.S. Cl. ..................................... 358/93; 358/107; 358/125; 358/185; 351/7
[58] Field of Search ............... 358/107, 105, 104, 125, 358/93, 185; 351/7

[56] References Cited

U.S. PATENT DOCUMENTS

| 3,583,794 | 6/1971 | Newman | 351/7 |
| 3,992,087 | 11/1976 | Flom | 351/7 |
| 4,034,401 | 7/1977 | Mann | 351/7 |

OTHER PUBLICATIONS

Whittaker Corporation, "Eye Movement Monitor and TV Pupilometer System" 9-1-76.

Primary Examiner—Robert L. Griffin
Assistant Examiner—Edward L. Coles
Attorney, Agent, or Firm—Thomas Langer

[57] ABSTRACT

An apparatus is disclosed for testing the eye movements of a viewer in response to visual stimuli, such as an advertisement, displayed on a screen. One camera cooperates with a light source to detect eye movements indicated by a light beam deflected off the viewer's cornea. Another camera is placed parallel to the screen and in front of the viewer. A right-angle lens directs light from the screen into the camera. The outputs of the two cameras are combined to superimpose the viewer's eye movements on the images displayed on the screen. A running time starting with the instant the advertisement is exposed to the viewer is also combined with the eye movement and screen presentations.

25 Claims, 3 Drawing Figures

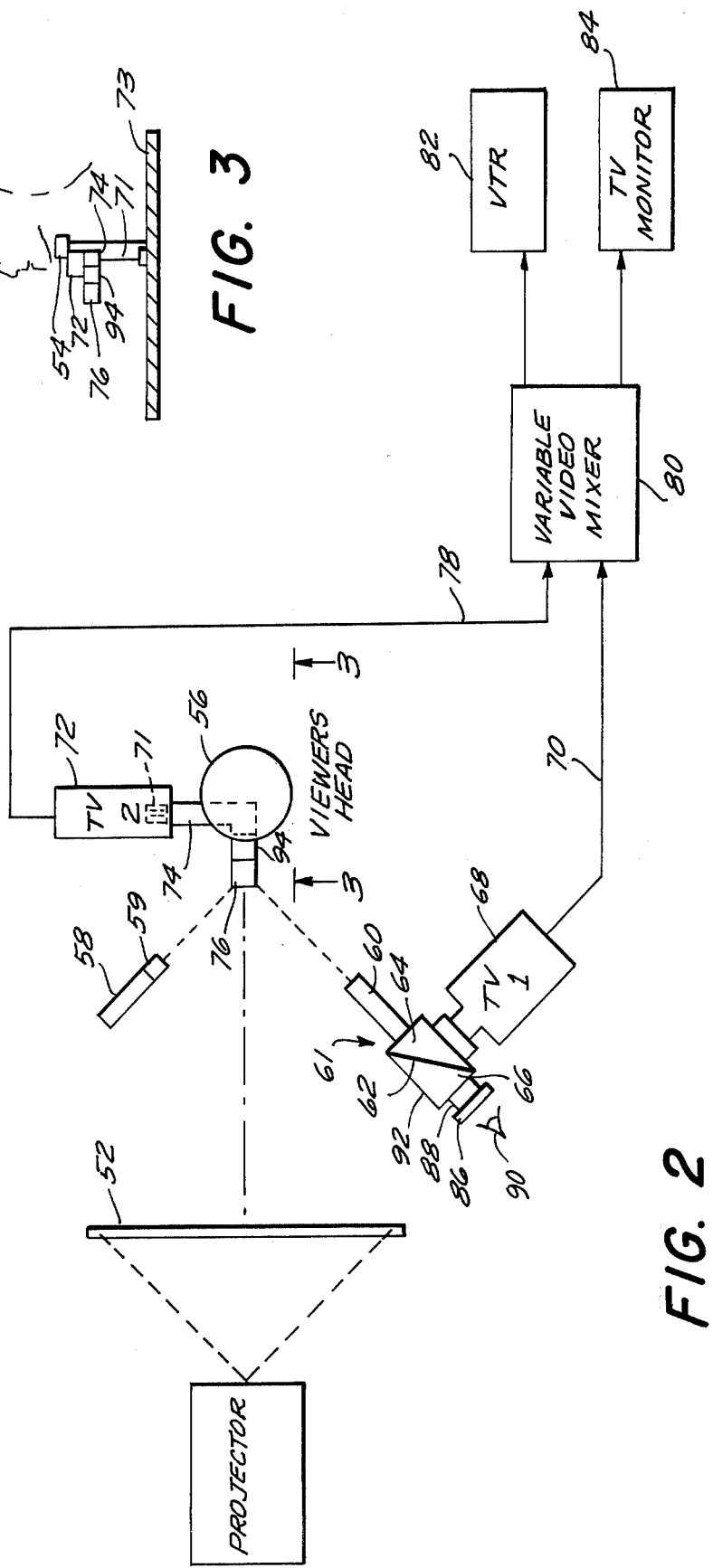

EYE MOVEMENT MONITORING APPARATUS

BACKGROUND OF THE INVENTION

The present invention relates to a testing apparatus, and more particularly to an arrangement for monitoring the eye movement of a viewer exposed to a given visual stimulus, such as an advertisement.

Advertising is regarded now and in all probability will continue to be so regarded as an important and highly useful service to generate and stimulate public interest in the advertised product. The spread of mass communications media in this country and abroad in the forms of newspapers, magazines, radio and television provide a convenient, effective avenue, for a price, to reach large numbers of people. Huge sums of money are expended on advertisements both on a national and local level and these, in turn, may have an impact on even significantly greater sums. The costs involved in the establishment of an advertisement campaign are willingly shouldered in the hope that it will have a favorable effect on profits. Much time, effort and thought are put into devising the various facets of advertising to maximize the benefits derived from the investment. One such facet concerns directing the campaign at the segment of the public believed to be the most likely targets for the advertised product. Thus, for example, if the product is more likely to be bought by a particular age group or profession or sex, the advertising medium catering to these people is chosen. Similarly, the content, form and presentation of the advertisement form another facet of advertising which receives considerable care and attention since, in the final analysis, it is the decisive factor in whether the product appears attractive enough to be distinctly remembered by the consumer while shopping. However, no matter how much effort, experience, and expertise are involved in the preparation of an advertisement, there is always the risk that it will miss its mark and fail to achieve its goal partially or even completely. This is due to the fact that the anticipated effectiveness of the advertisement is based on the opinions of those whose prepare it and these may not always coincide with its actual effect on the "typical" or "average" consumer. Since the expenditures on advertisements are so high, it is clearly highly desirable to minimize these risks. Some efforts to this end have taken the form of obtaining feedback from the public by way of preliminary selected samplings of viewer opinions for analysis and appropriate action before the full advertisement campaign is authorized. This permits the advertiser to ascertain whether the various facets of the advertising campaign are producing satisfactory results so that any existing problems can be eliminated and corrected at relatively low cost.

This aspect of advertising involving preliminary investigation is characterized by ever increasing sophistication. Its beneficial value is well established and efforts to improve its techniques and thereby add to its usefulness are being continuously made. One area of preliminary investigation which has come to the fore in recent years concerns the second above discussed facet of advertising and is based on monitoring the eye movements of a viewer who is watching an advertisement. Analysis of such eye movements supplies valuable information about whether the viewer's attention is sufficiently attracted to those portions of the advertisement which are considered of greatest value in selling the advertised product. Thus, for example, it can be determined whether a photograph showing, say, a brilliant sunrise as background to the product placed in a corner of the picture attracts the viewer's attention to one or the other. If his attention is only briefly drawn to the product and then dwells on the sunrise, it is unlikely that the product has made a memorable impression on him. However, if the sunrise serves to initially attract his attention to the advertisement and his gaze then settles on the product, chances are good that he will remember the product which, in turn, may lead him to purchase it. This is a highly simplified discussion of the analysis done, but it serves to illustrate the valuable contributions of this technique. The same benefits can be derived for movie type advertisements projected on a suitable screen. For purposes of this presentation all such advertisements which may be in the form, for example, of movie film or video tape, will be referred to as movie film. The analytical difficulties, however, are multiplied. This is because the viewer is seeing an ever changing image and each scene of the commercial (as this type of advertisement is commonly called) must contribute satisfactorily to the desired effect. Thus, many scenes must be analyzed, instead of just one as is the case with the photograph advertisement, so that any defects found in a particular scene or in how it coordinates with the rest of the commercial can be corrected. Synchronization for properly recording the view's reactions and what he sees is an essential ingredient not necessary, of course, with the photograph advertisement. Also, greater skill is required to interpret the results of the eye monitoring because of the variables involved.

This eye monitoring technique for preliminary advertisement effectiveness investigation has been in use for some time. Typically, the subject viewer is shown the advertisement and his visual reactions are recorded for subsequent detailed analysis. Should this analysis reveal certain deficiencies, appropriate corrections can be made. In the above-presented example, the correction might be to increase the picture-size of the product or to move it from the corner to the center in order to increase its attraction to an impression on the viewer.

A known apparatus for obtaining the necessary data for this technique is depicted in FIG. 1. The viewer, represented by eye 1, sees an image shown on screen 3 by a rear projector 5. The viewer's head is secured in an apparatus (not shown) so that he can scan the entire screen only by moving his eyes. Projector 5 can be a slide projector or movie projector depending on the type of advertisement and screen 3 can be a projection screen or the screen of a television (TV) set in which case a TV camera (not shown) transmits to the TV set the image picked up from the projector. The remainder of the apparatus serves to sense and record the viewer's eye movements in relation to what he is seeing. More specifically, light source 7 reflects a thin beam of light, 9, off the cornea of the eye. Reflected beam 9' enters light-collection tube 11 of an assembly 12. The beam exiting tube 11 is the size of a dot. Tube 11 includes the optics required to focus the beam properly and maximize its brightness. A filter 13 is preferably placed on light source 7 to produce a red beam because this color is least annoying to the viewer.

Light beam 9' exiting tube 11 encounters semi-transparent silver surface 15 secured between prisms 16 and 18. This mirror-like surface is designed to transmit part of the beam while reflecting the other part. The reflected part of beam 9' passes through a suitable optic 17 and into a TV camera 19. The video signal is recorded on video tape by recorder (VTR) 21 and may simultaneously be displayed on TV set 23 for immediate monitoring. As the viewer's eye scans the projected image, the beam 9 is correspondingly deflected by the cornea so that TV camera 19 can pick up a dot representative of the precise eye location.

The above arrangement suffices to monitor eye movements when the viewer is shown a photograph. For later analysis, all that needs to be done is to superimpose the photograph in a well known manner on the recorded eye movements. Using a slide projector and the VTR on the same screen, for example, is one way to do this. However, when a movie film advertisement is used, it is also essential to know what scene is being viewed as the eye moves to a particular point on the screen. Consequently, the depicted apparatus includes means for simultaneously recording the eye movement and the viewed scene. More specifically, semi-transparent mirror 27 is interposed between screen 3 and viewer 1. It transmits a portion of the light from screen 3, as represented by beams 29 and 31, to viewer 1 and reflects part of beams 29 and 31 to a standard mirror 33. Mirror 33, in turn, reflects this light toward semi-transparent mirror 15. Mirror surface 15 transmits part of this light to camera 19 which now picks up the reflected portion of beam 9' superimposed on the screen image from mirrors 27, 33 and 15.

Needless to say, all the mirrors must be carefully set to critical positions for the apparatus to function properly. The apparatus is calibrated as the operator peers through optic 35 at the transmitted part of beam 9' and the reflected part of beams 29 and 33 from mirror surface 15. The operator sees exactly what camera 19 sees. Beam 9' should be centered when the viewer is looking at the center of screen 3. If not, appropriate adjustment of the relative position of the mirrors is made, such as by movement of assembly 12, which may be placed on a track (not shown) for this purpose.

Inherent to the above-described apparatus are several salient disadvantages. Some of these render the task of the analyst more difficult due to the dim and blurred image the apparatus provides. The dimness of the projected image is attributable primarily to the light-splitting occurring in mirrors 27 and 15. Even a relatively bright projected image appears dim to camera 19. Image sharpness is adversely affected by the different reflective planes present in a semi-transparent mirror which may result in ghost images much like those found on a television set placed in a poor reception area. Image contrast is reduced by the mixing of two light sources in housing 18. This superimposition also reduces the dot brightness. To compensate for the latter, the intensity of light source 7 must be increased but at the cost of possible discomfort to the viewer. In addition to all of the above, if a large screen 3 were to be used, its periphery would not be viewable through mirror 27 and, therefore, this portion of screen 3 will not be picked up by camera 19. Consequently, the analyst cannot know what the viewer is looking at when the area is involved.

Besides complicating the analyst's task, this apparatus is not satisfactory from the viewer's standpoint either. Since the brightness of the projected image is dimmed by mirror 27, the viewer may have to strain in order to see some parts of the advertisement, particularly those in which the light level for certain scenes is somewhat lower. Also, since the size of mirror 27 is fixed for a particular screen size, should a larger screen size be desirable, the screen periphery would be outside the viewing area of mirror 27, as mentioned above. The support frame (not shown) for mirror 27 would thus block part of the screen. Moreover, mirror 33 would also block part of screen 3 should such a larger screen size be desirable. Furthermore, since critical mirror alignment is necessary, the viewer's eyes must be within certain confines due to the limited range of adjustment of such a system. Thus, a tall person must keep his head in basically the same position as a shorter person thereby causing physical discomfort, particularly should the interview be a lengthy one. These deficiencies of the apparatus singly or in combination may comprise an annoyance factor to the viewer sufficient to significantly distort his reactions due to either his inability to see possibly important parts of the advertisement or to the distractions such blockages may cause.

Though at first glance it may appear that the above-discussed problem could be easily overcome by simply moving mirror 27 and/or mirror 33, practicality dictates otherwise. The mirrors must be aligned within certain critical tolerances. To maintain this alignment, the mirrors are mounted on a support base (not shown) which is rather heavy and bulky because it needs to be strong and solid. Were it designed for adaptibility to various screen sizes, its size and weight would be even greater. Since portability, cost, and ease of operation of the apparatus are important considerations should it have to be taken to the viewer rather than vice versa, such provisions are unsatisfactory. In fact, even the support base used in the above discussed apparatus with limited versatility unacceptably reduces the portability of the equipment.

The problems which the apparatus presents to the viewer are a primary cause for its limited usefullness in other respects as well. Thus, because a mirror 27 obscures some parts of a screen larger than the one shown in FIG. 1, the flexibility of the apparatus to show various advertisements with equal effectiveness is sharply curtailed. For example, to ease eye strain it is desirable to test a printed advertisement on a larger screen to facilitate reading. Also, resolution of the eye movements may be enhanced by a larger screen size. This can be important for any advertisement, of which the printed kind is an example, in which fine detail is involved. Furthermore, due to the eye curvature of some people, the dot position of the reflected beam 9' when the viewer is looking at a corner of screen 3 registers off the screen when the dot is superimposed on the screen in housing 18. This overshoot causes analytical uncertainties since it is impossible to determine with precision what the viewer is looking at in such a situation, and no adequate adjustment is available in the apparatus.

SUMMARY OF THE INVENTION

It is, therefore, a general object of the present invention to provide a new and improved eye movement monitoring apparatus.

A more specific object of the present invention is to provide a flexible eye movement monitoring apparatus readily adaptable for different screen sizes and for the physical characteristics of different viewers.

A further object of the present invention is to provide an arrangement which facilitates the portability of an eye movement monitoring apparatus.

Another object of the present invention is to provide an eye movement monitoring apparatus which generates a bright, sharp image of the screen and of the viewer's eye movements.

Still another object of the present invention is to provide an apparatus which facilitates and simplifies the analyst's task.

In accordance with these and other objects of the invention, an apparatus is provided in which the problematical mirror system and the heavy base are eliminated and replaced by an arrangement which according to the preferred embodiment utilizes two cameras and a specially adapted lens. More specifically, one camera monitors the viewer's eye movements while the other camera monitors the screen. The latter camera is placed parallel to the screen to keep it out of the way of the viewer who would otherwise bump into or at least be discomfited by it due to its size. A right angle lens receives light from the screen and reflects it into the camera. This lens is mounted below the viewer's field of vision and as close as practicable to the viewer's eye to reproduce what the viewer sees. A zoom capability on this lens enables easy adjustment of screen size to compensate for the overshoot problem presented by some viewers.

The preferred embodiment also included a running-time display visible through the screen monitoring apparatus. This display is triggered at the instant an advertisement is exposed to the viewer and serves to greatly facilitate the determination of the amount of time spent by the viewer on a particular portion of the screen.

BRIEF DESCRIPTION OF THE DRAWINGS

To the accomplishment of the above and to such other objects as may hereinafter appear, the present invention relates to an apparatus for testing the eye movements of a viewer in response to visual stimuli, as defined in the appended claims and as described in this specification, taken together with the accompanying drawings, in which:

FIG. 2 is a schematic plan view of an apparatus constructed in accordance with the present invention; and FIG. 3 is a side elevational view taken along lines 3—3 in FIG. 2 showing the location of the camera and lens combination in relation to the viewer's head.

DETAILED DESCRIPTION OF THE DRAWINGS

Figure 1:
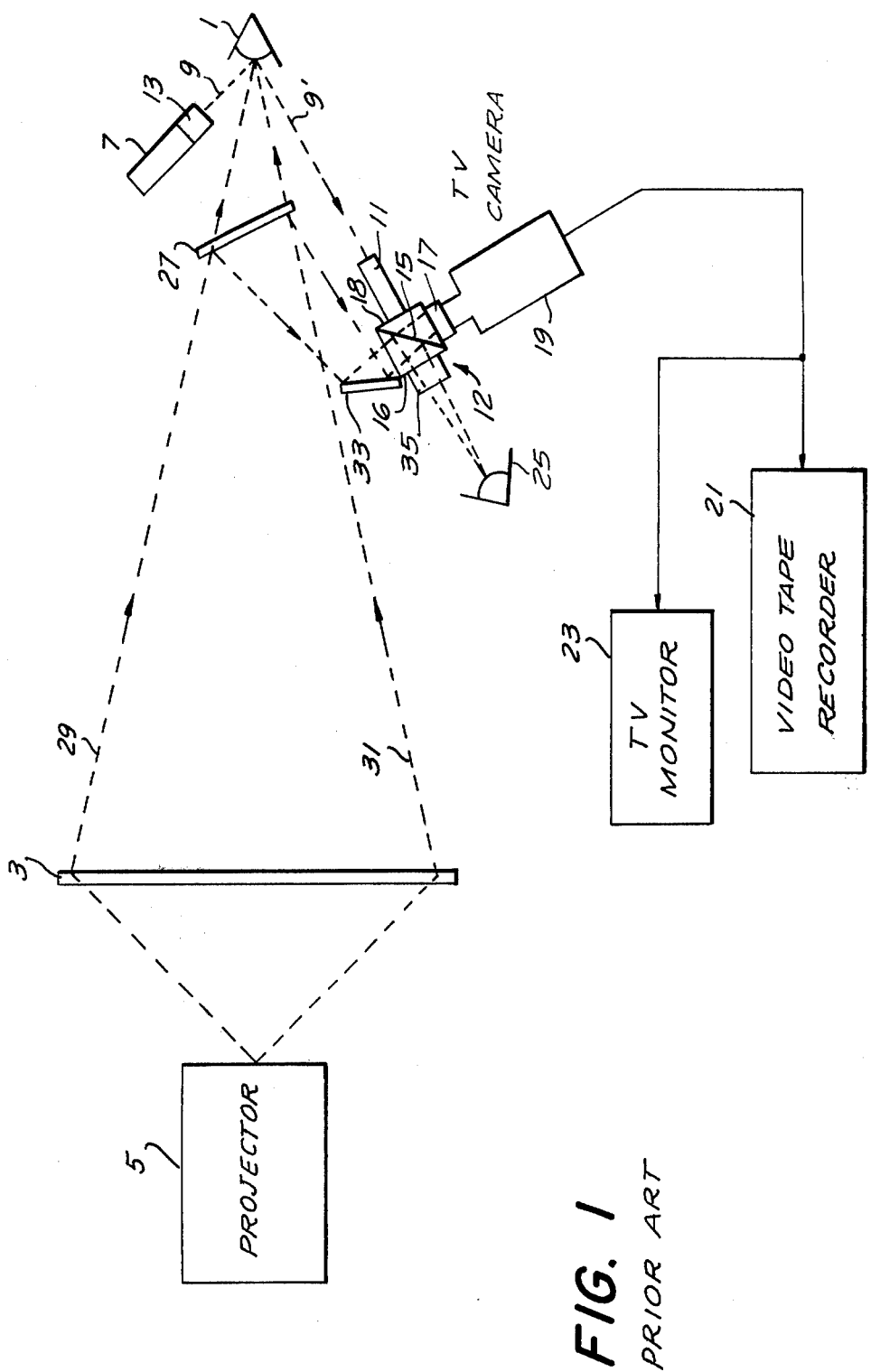
FIG. 1 is a schematic diagram of a prior art eye monitoring apparatus, as described in detail above.

As best shown in FIG. 2, projector 50 displays some form of visual stimuli on screen 52. The projector can be a movie projector, a slide projector, a television set or any device for displaying an image and screen 52 will, of course, be appropriate for cooperating with the chosen type of projector. In the preferred embodiment, a television set is used to display an image detected by a suitable camera (not shown).

At a preselected distance from screen 3 is secured a head support in the form of a chin rest 54 (see FIG. 3). It serves to hold the head 56 of the viewer in a fixed position during the eye monitoring procedure. The use of further head restraints such as a forehead support bar (not shown) is optional. Light souce 58 emits a thin light beam through a filter 59 (preferably producing a red beam) which bounces off the viewer's cornea into light collection tube 60 on an assembly 61. The deflected beam proceeds to a semi-transparent, mirror-like surface 62 secured between prisms 64 and 66. Mirror 62 reflects this light beam into television camera 68 to generate a dot image. Since the position of the viewer's eye determines the position of the dot, output 70 of camera 68 provides an indication of viewer eye movement.

Since, as discussed above, it is often desirable to superimpose the viewer's eye movements on the image being shown, particularly during a commercial test, a means must be provided for monitoring the screen. The difficulties and disadvantages encountered by previous attempts to this end are overcome by the novel arrangement of the present invention. Specifically, an assembly 69 is fixed by support 71 to a base 73. Assembly 69 comprises television camera 72 which is placed slightly in front of the viewer's torso and facing in a direction parallel to screen 52. Right-angle lens 74 is attached to camera 72 and points directly at screen 52. In an effort to duplicate the viewer's field of vision, lens 74 is placed as closely as possible to the viewer's eyes. As best seen in FIG. 3, it is placed underneath the viewer's chin and aligned in substantially the same vertical plane as the viewer's eyes. As its name clearly implies, right-angle lens 74 deflects the light beams from screen 52 90° into camera 72. A further important feature of this arrangement is a zoom lens 76 attached to lens 74 which is used to change the size of screen 52 detected by camera 72.

Output 78 of camera 72 and output 70 of camera 68 are combined in a video mixer 80. The relative intensities of the two outputs is variable so that the mixer can selectively emphasize one or the other at its output. A video tape recorder (VTR) 82 can be used to record the superimposed eye movement and advertisement signals for later analysis. Furthermore, a television monitor 84 serves to provide the operator with an immediate presentation of the test results.

To initially calibrate the apparatus, cap 86 is removed from optic 88 and operator 90 peers into it. The viewer is requested to look at the center of screen 52 and the operator suitably adjusts the position of assembly 61 until the dot seen by the operator is also centered. Assembly 61 is movable toward and away from the viewer as well as up and down by a conventional screw-type movement which is not shown in order to obtain clarity and conciseness of presentation. The view is then requested to look at a corner of screen 52. If the dot appearing on monitor 84 does not land precisely on the corner, zoom lens 76 is used to make the necessary correction. It can increase screen size should eye overshoot be detected and conversely it can decrease screen size should the problem be eye movement undershoot. Once these simple, straight-forward alignments have been completed, the operator may adjust the mixer 80 so that the requisite relative dot intensity appears on the screen image.

It will be apparent from all of the above that several significant, valuable advantages over the prior art are attributable to the present invention. Firstly, the complicated, unwieldy and obtrusive mirror system has been eliminated. Since the light from source 58 and screen 52 must no longer pass through several semi-transparent mirrors, a much brighter image of the dot is picked up by camera 68. Although surface 62 is used as a semi-transparent mirror during the calibration procedure, at all other times its reflectivity characteristics are maximized by sealing the sides of assembly 61 which do not receive or transmit light. Thus, side 92 is permanently sealed and optic 88 is normally covered with cap 86. Similarly, loss of brightness is minimized with the screen monitoring apparatus since nothing interferes with the efficient operation of zoom 76 and right angle lens 74 to transmit substantially all the received light to camera 72. The elimination of the mirrors also provides a sharper picture since the many reflective planes discussed above are no longer involved. Moreover, since an electronic superimposition in mixer 80 rather than an optic one in assembly 61 occurs with the dot and screen images, a good contrast is attained. Clearly, then, the picture quality available at VTR 82 and/or monitor 84 is noticeably brighter and sharper than heretofore possible with the above-described prior art apparatus.

A further important advantage of the apparatus not to be overlooked is enabled by zoom lens 76. If the periphery of the dot movement corresponding to deflection of the beam off the viewer's eye does not coincide with the periphery of screen 52 when the two are superimposed, a simple turn of the zoom suffices to correct this previously problematical difficulty. The operator merely requests the viewer to look at a corner of screen 52 and, while checking monitor 84, adjusts zoom lens 76 until the projected screen coincides with the viewer's eye deflection characteristics. Besides serving this eye-characteristic compensation, the zoom lens also enables use of a variety of screen sizes with only a minor adjustment of the zoom being necessary.

The novel apparatus of the present invention also adds to the comfort and convenience of the viewer. Since a critical mirror adjustment is no longer a consideration, the viewer's eye level can easily be changed to accomodate viewers of different heights by simply changing the height of chin support 54. Assembly 61 and possibly light source 58 are then adjusted correspondingly. The position of camera 72 and lens 74 may also be slightly adjusted to maintain the latter as close to the viewer's eyes as possible although this is normally unnecessary. In addition, since mirror 27 of FIG. 1 has been eliminated, the viewer's line of sight is completely unobstructed and unimpaired. Thus, even a relatively dim image on screen 52 will appear sufficiently bright since the light is not attenuated by mirror 27. Furthermore, a variety of screen sizes can be used without any need to adjust anything as far as the viewer is concerned. (Of course zoom lens 76 does need adjustment, as discussed above.)

Two additional points remain to be made. As to the first point, the use of the two camera system is made feasible by the specific positioning of camera 72 and the usage of lens 74. Since the combined length of camera 72 and zoom lens 76 is greater than one foot, were the camera aimed directly at screen 52, it would jut out toward the viewer if the position of the lens directly below the viewer's eyes were to be maintained. This obviously would cause unacceptable discomfort to the viewer. If the camera were pushed forward or placed beside or behind the viewer's head to ameliorate the situation, the lens would no longer be directly below the viewer's eyes and a distorted picture of what is actually seen by the viewer would be available to the analyst because of an improper angle of view. Of course, this could be corrected somewhat by moving the screen further away from both the viewer and camera 72 but this is prohibited by spacial limitations. The apparatus should be as compact as possible so as to fit into a small area so that a maximum number of such devices can be installed in a room. This enables interviewing several viewers simultaneously so that test results for a particular sampling can be obtained and analyzed as quickly as possible. Also, to enhance the portability of the equipment so that it can easily be transported to the viewer, the equipment may for example be installed in a vehicle, such as a van, where space is at a premium. Because of the spacial requirements encountered in the testing environment, the particular placement of the camera and the use of a right angle lens according to the present invention have been key elements in making the apparatus practicable. Now, as to the second point, since all the equipment component are easily adjustable and thus critical alignment need not be continually maintained, as was the case with the mirrors, no heavy base is needed. The apparatus can be packed in a relatively small container and then easily afixed to any support, such as a table top, by any convenient securing means such as suction cups for example. Should such portability be required, this apparatus can provide it.

One further feature of the present invention greatly simplifies the analyst's task. Previously, in determining how much time a viewer spent watching a particular portion of the screen, the analyst used a stopwatch to record the time when the viewer's eye shifted from one position to another. Were the analyst to make a slight error on each reading, these errors could accumulate and have a serious impact on the results when one considers that hundreds of such readings may be taken for each advertisement. To minimize this problem, the analyst resets the stopwatch to zero and returns to the beginning of the recorded test after each reading. This obviously consumes a great deal of time and increases the cost of the service.

To eliminate the need for repetitively resetting the stop-watch, a timing module 94 is fixed between zoom lens 76 and right angle lens 74. Its time output is visible through lens 74 and thus camera 72 records the running-time of the advertisement along with the advertisement itself as displayed on screen 52. Any suitable triggering means can start the timing display either manually or automatically in synchronism with projector 50 so that the running-time begins when the viewer is first exposed to the advertisement. For example, the timing module can respond to a mark on the projected film or video tape. The display itself can be positioned anywhere along the periphery of the picture seen on, say, monitor 84 so as to be least obtrusive. With this feature, no analyst-reaction-time error is involved since one can tell exactly when the viewer's eye shifts position since the time it occurs is displayed right on monitor 84. Accuracy is maximized, analysis time is minimized, and costs are lowered with the use of the timing module in this manner.

While but a single embodiment of the present invention has been here specifically disclosed, it will be apparent that many variations may be made therein. For example, timing module 94 need not be placed as disclosed but anywhere it would be visible through camera 72. In fact, it could cooperate with camera 68 instead. Also, cameras 68 and 72 have been disclosed as television cameras but these could be movie film cameras appropriately synchronized and the superimposition could be done on film rather than electronically or by a combination of the two techniques. Furthermore, the positions of optic 88 and camera 68 could be switched. These and other such changes are all within the spirit and scope of the invention as defined by the following claims.

I claim:

1. Apparatus for determining the eye movements of a viewer in response to visual stimuli comprising:
   a screen for displaying said stimuli;
   support means placed at a preselected distance in front of said screen for maintaining the viewer's head in a relatively fixed position;
   means for monitoring the viewer's eye movements;
   means for monitoring said stimuli displayed on the screen and placed in front of the torso of said viewer, said stimuli monitoring means extending generally parallel to said screen;
   lens means aimed at said screen and attached to said stimuli monitoring means adjacent said support means and below viewer eye level for receiving light from said screen and for transmitting it into said image monitoring means; and
   means for combining the outputs of both said monitoring means to superimpose the viewer's eye movements on the displayed stimuli.

2. The apparatus of claim 1, wherein both of said monitoring means are television cameras and wherein said combining means comprises a variable video mixer.

3. The apparatus of claim 1, further comprising a timing means for providing to said combining means a running-time indication from the instant the visual stimuli are displayed to the viewer.

4. The apparatus of claim 1, wherein said combining means displays the running time superimposed on the outputs of both said monitoring means.

5. The apparatus of claim 1, wherein said lens means comprises a right angle lens.

6. The apparatus of claim 5, wherein said visual stimuli are comprised of movie film type scenes.

7. The apparatus of claim 6, wherein both of said monitoring means are television cameras.

8. The apparatus of claim 7, wherein said combining means comprises a video mixer.

9. The apparatus of claim 8, wherein said combining means comprises a variable video mixer.

10. The apparatus of claim 9, wherein said lens means includes a zoom lens.

11. The apparatus of claim 10, further comprising a timing means for providing to said combining means a running-time indication from the instant the visual stimuli are displayed to the viewer.

12. The apparatus of claim 11, wherein said lens means is positioned directly below said viewer's eyes.

13. Apparatus for monitoring the eye movements of a viewer in response to visual stimuli and for measuring the amount of time spent by the viewer's eye in a given position comprising:
   a screen for displaying said visual stimuli;
   means for monitoring said screen;
   means for monitoring the viewer's eye movements in response to said visual stimuli;
   timing means for providing a running time indication from the instant the visual stimuli is displayed to the viewer; and
   means for displaying the superimposed outputs from both of said monitoring means and said timing means.

14. The apparatus of claim 13, wherein both of said monitoring means are television cameras.

15. The apparatus of claim 14, wherein said timing means is a timing module attached to the camera lens of one of said monitoring means and having its time display visible through said lens.

16. The apparatus of claim 15, wherein said timing module is attached to and visible through the camera lens of the visual stimuli monitoring means.

17. The apparatus of claim 16, further comprising trigger means to actuate said timing means at the instant the visual stimuli is displayed to the viewer.

18. The apparatus of claim 13, wherein said timing means has its display in the field of view of one of said monitoring means.

19. Apparatus for testing the visual response of viewer to a visually displayed advertisement, comprising:
   a. a screen for displaying said advertisement;
   b. means for monitoring the eye movements of said viewer in response to the displayed advertisement;
   c. a television camera placed in front of said viewer and generally parallel to said screen;
   d. a right-angle lens attached to said camera and positioned substantially directly below the eyes of said viewer and aimed at said screen; and
   e. means for combining the outputs of said monitoring means and said television camera to superimpose the eye movements of said viewer on said advertisement.

20. The apparatus of claim 19, further comprising a timing means visible through said television camera for providing a running time from the instant said advertisement is exposed to the viewer.

21. The apparatus of claim 19, wherein said advertisement is of the movie film type.

22. The apparatus of claim 19, wherein said screen is that of a television set.

23. The apparatus of claim 22, further comprising support means for maintaining the head of said viewer in a fixed position.

24. The apparatus of claim 23, further comprising a timing means visible through said television camera for providing a running time from the instant said advertisement is exposed to said viewer.

25. The apparatus of claim 24, wherein said advertisement is of the movie film type.

* * * * *